United States Patent [19]
Tuite

[11] Patent Number: 5,865,780
[45] Date of Patent: Feb. 2, 1999

[54] TRANSPORTABLE CERVICAL IMMOBILIZATION DEVICE

[75] Inventor: Gerald F. Tuite, Houston, Tex.

[73] Assignee: SDGI Holdings, Inc., Wilmington, Del.

[21] Appl. No.: 543,073

[22] Filed: Oct. 13, 1995

[51] Int. Cl.⁶ .................................................. A61F 5/00
[52] U.S. Cl. .............................. 602/32; 128/870; 5/628
[58] Field of Search ..................................... 128/845, 846, 128/869, 870, 875, 874, 876; 602/32–39; 5/637–640, 622, 621, 623, 624; 606/61

[56] References Cited

U.S. PATENT DOCUMENTS

| | | | |
|---|---|---|---|
| 2,376,507 | 5/1945 | Ruther | 5/628 |
| 3,732,863 | 5/1973 | Harrington | 5/628 |
| 4,444,179 | 4/1984 | Trippi | 128/75 |
| 4,463,758 | 8/1984 | Patil | 5/637 |
| 4,473,912 | 10/1984 | Scheidel et al. . | |
| 4,489,715 | 12/1984 | Hall . | |
| 4,519,106 | 5/1985 | Sandquist | 5/82 R |
| 4,539,979 | 9/1985 | Bremer . | |
| 4,541,421 | 9/1985 | Iversen et al. . | |
| 4,566,445 | 1/1986 | Jelsma et al. . | |
| 4,612,930 | 9/1986 | Bremer . | |
| 4,620,530 | 11/1986 | Lanier et al. . | |
| 4,640,275 | 2/1987 | Buzzese et al. . | |
| 4,735,196 | 4/1988 | Krag et al. . | |
| 4,765,317 | 8/1988 | Eastman et al. . | |
| 4,854,305 | 8/1989 | Bremer . | |
| 4,890,605 | 1/1990 | Rosendale . | |
| 4,913,135 | 4/1990 | Mattingly | 128/78 |
| 4,934,354 | 6/1990 | Anapliotis . | |
| 4,987,892 | 1/1991 | Krag | 606/61 |
| 5,010,881 | 4/1991 | Boudreau et al. . | |
| 5,016,620 | 5/1991 | Matthews . | |
| 5,027,833 | 7/1991 | Calkin . | |
| 5,042,462 | 8/1991 | Bremer . | |
| 5,062,415 | 11/1991 | Weatherby et al. . | |
| 5,063,920 | 11/1991 | Moore | 128/DIG. 19 |
| 5,067,483 | 11/1991 | Freed . | |
| 5,086,757 | 2/1992 | Lestini . | |
| 5,121,741 | 6/1992 | Bremer et al. . | |
| 5,156,588 | 10/1992 | Marcune et al. . | |
| 5,195,947 | 3/1993 | Bode . | |
| 5,211,185 | 5/1993 | Garth et al. . | |
| 5,261,873 | 11/1993 | Bremer et al. . | |
| 5,265,625 | 11/1993 | Bodman . | |
| 5,302,170 | 4/1994 | Tweardy . | |
| 5,334,133 | 8/1994 | Carroll . | |
| 5,342,290 | 8/1994 | Schuellein . | |
| 5,360,393 | 11/1994 | Garth et al. . | |
| 5,370,605 | 12/1994 | Weed . | |
| 5,388,580 | 2/1995 | Sullivan et al. . | |

FOREIGN PATENT DOCUMENTS

| | | |
|---|---|---|
| 2 127 144 | 9/1972 | France . |
| 2 205 815 | 5/1974 | France . |
| 2 290 184 | 4/1976 | France . |
| 2 414 911 | 8/1979 | France . |
| 2 430 762 | 2/1980 | France . |
| 2 524 799 | 10/1983 | France . |
| 2 524 800 | 10/1983 | France . |

*Primary Examiner*—Michael A. Brown
*Attorney, Agent, or Firm*—Woodard, Emhardt, Naughton, Moriarty & McNett

[57] ABSTRACT

A transportable, diagnostic and surgical procedure patient support board (10) compatible for use with CT, X-ray and MRI machines includes a rectangular board to which the patient is secured, tracks (21) along the head end and partially along the sides of the board, and clamps (22) made of a non-ferromagnetic material mounted adjustably on the tracks which support traction gear and immobilization rods (45–48) that extend to a halo on the head of the patient. Various configurations of rods and adjustable clamps are disclosed.

25 Claims, 5 Drawing Sheets

TRANSPORTABLE CERVICAL IMMOBILIZATION DEVICE

FIELD OF THE INVENTION

This invention relates in general to a transportable medical device used for a patient with cervical spine instability. In particular this invention relates to a radiolucent board and its component parts, which provide continuous cervical spine immobilization during all phases of acute medical treatment of cervical spine instability, including transport, diagnostic testing and operative procedures. Additional attachments to the board allow the patient to be placed in cervical traction on the board.

BACKGROUND OF THE INVENTION

Cervical spine instability can cause permanent spinal cord damage. Trauma victims, as well as other patients with suspected cervical spine injury, should be immobilized during examination and diagnostic testing to reduce the risk of exacerbating a cervical spine injury. If cervical spine instability is confirmed on exam, the management of such injury depends on rapid realignment and rigid immobilization of the neck. Placing the patient in cervical traction may be necessary to reduce a fracture of the cervical spine. Once reduced, the fracture or other instability should be continuously immobilized to prevent further injury until a course of treatment can be completed. Often treatment will require a surgical procedure to fuse the unstable portion of the cervical spine.

A heightened awareness of, and a greater attention to, the maintenance of cervical immobilization has vastly improved patient care. Neck immobilization devices are currently available for each step of the management of cervical spine injuries, from initial immobilization to diagnostic tests, to the surgical fusion and the long-term immobilization often needed to promote effective healing. However, known devices are each limited in their application to only a portion of the diagnostic and treatment process. For example, the devices shown in U.S. Pat. Nos. 5,027,833; 5,016,620; 4,566,445; 4,529,106; 4,519,106 and 4,473,912 all relate to spinal boards which are applied at the scene of a traumatic injury, often in conjunction with a cervical collar or other head immobilization device, to facilitate the transport of the accident victim to a hospital. Some of these devices are designed to be radiolucent, but none provide an integrated system for placing the patient in rigid cervical immobilization once cervical instability is diagnosed. Additionally, none of these devices is designed to immobilize the patient during surgical procedures. U.S. Pat. No. 4,854,305 describes a transportable, radiolucent board that includes a traction device. However, this device does not offer the ability to place the patient in rigid cervical immobilization and is not designed for use during surgery.

When cervical instability is diagnosed, it should be reduced under radiographic guidance. Once the cervical fracture has been reduced, halo fixator devices are commonly used to rigidly immobilize the cervical spine until treatment is complete. In general, a halo device consists of a metal circlet (the halo) which surrounds the patient's head and is attached directly to the skull by a number of screws. The halo is fixedly attached to a rigid plastic vest on the patient's torso by metal bars, which run from the vest to a "head block" that is attached to the halo. The patient's head is thus immobilized relative to his or her torso, so that no cervical spine movement is possible. U.S. Pat. Nos. 5,156,588; 5,063,920; 5,010,881; 4,913,135; 4,735,196; 4,620,530; and 4,541,421 all describe various halo fixation devices. Such devices provide a transportable system for cervical immobilization, but their use is often impractical in the acute situation because halo vests have a size specification that should match the individual patient, and thus a proper vest may not be readily available. Furthermore, the vest should only be applied by a physician experienced in its use, and its placement limits health care workers' access to the patient's back, chest and abdomen. These issues are important in connection with the trauma patient, whose treatment must be expeditious and who also often has associated injuries that require medical access to the entire body. Additionally, if cervical immobilization is obtained by using a halo vest, it may be compromised during surgical procedures, because the vest must often be removed to allow greater surgical access to the patient's torso.

U.S. Pat. No. 5,063,920 describes a device that immobilizes a patient wearing a halo vest by attaching the posterior halo support rods to the patient's bed. The anterior support rods remain attached to the anterior section of the halo vest, but the posterior portion of the vest can be removed. However, this device does not allow for patient transport, is not radiolucent, does not provide unimpeded access to the patient's body, is not intended for use in surgical procedures and does not provide a means of cervical traction.

Numerous devices also exist which are designed to impart traction to the cervical spine. U.S. Pat. Nos. 5,195,947; 5,067,483; 4,890,605; 4,489,715; 4,539,979 each describe a type of traction device. Some of these are meant to be transportable and/or radiolucent, but none is designed as a part of an integrated system that allows traction, immobilization, transport and surgical access, as provided by the present invention.

The above-described devices may all be useful during certain stages of the acute management of a patient suspected of having a cervical spine injury, but the interruptions in immobilization resulting from limitations on their use can pose dangers to the patient. Especially in trauma patients, who may have multiple injuries, extensive diagnostic testing is often required. Such testing often requires patient transportation to several different locations, which can present difficulties if the patient requires cervical traction to maintain alignment of a cervical fracture. The traction device is usually attached to the patient's stretcher or some other traction bed, and removal of the traction is often necessary to move the patient onto the diagnostic testing machine.

Therefore, it is often necessary to repeatedly move patients among stretchers, dollies, testing tables, operating tables, and so forth, without adequate cervical support. During such moves, cervical immobilization is often lost or compromised, which can result in the loss of cervical alignment of the unstable spine and lead to further spinal cord damage and permanent neurologic injury.

The need for continuous cervical immobilization continues beyond the diagnostic testing phase because cervical instability often requires surgical treatment to fuse the spine. Halo fixation devices are often used during such surgery to maintain cervical immobilization. However, these devices restrict surgical access to the patient's body, complicating the harvest of bone needed for fusion and other procedures. In addition, in the trauma patient who often has significant life-threatening injuries in addition to cervical instability, a halo fixation system can be an impractical cervical immobilization device because it may prevent surgical access to the site of emergent injuries, which often are located on the abdomen, chest and back of the patient.

A general object of the present invention is to provide a new and improved transportable cervical immobilization device that obviates each of the problems in prior devices noted above.

Another object of the present invention is to provide a new and improved immobilization device of the type described that eliminates dangerous periods of cervical instability occasioned in moving the patient by providing an adjustable, transportable cervical immobilization device that can be used in each stage of the acute management of cervical instability, allowing rapid and secure transport from the emergency room, to the radiology department, to the operating room, and finally to the patient's recovery room.

Still another object of the present invention is to provide a new and improved device of the type described that provides rigid cervical immobilization during surgery, while providing unimpeded surgical access to the patient's torso and the option of using radiographic guidance intraoperatively.

Yet another object of the present invention is to provide a new and improved immobilization device that includes a means of attaching and/or removing cervical traction without having to remove the patient's cervical immobilization supports to do so.

SUMMARY OF THE INVENTION

These and other objectives are attained in accordance with the present invention through the provision of an immobilization device that includes a rigid board made of lightweight, radiolucent material with attachable non-ferromagnetic components which fit to the board to create an adjustable, transportable, non-ferromagnetic cervical immobilization device which can be used in the comprehensive diagnostic and surgical management of cervical spine instability. Additional components attach to the board to allow the patient to be placed in cervical traction. A patient suspected of having a cervical spine injury is secured to the board with a plurality of straps that attach to the board at slots cut in the interior of the board and along the sides thereof, such side slots also serving as handholds for lifting the board. These straps are crossed over the patient and secured by hook and loop fasteners forming an adjustable loop connection to the board, thereby immobilizing a patient's body on the board. When not in use, these straps may be removed for cleaning.

The head end of the board and the upper portion of the side edges of the board have a grooved tract designed to receive clamp components that are used when placing the patient in traction or in cervical immobilization. If cervical instability is diagnosed, the patient may be placed in cervical traction on the board. This is accomplished by first attaching the traction component of the invention to the head of the board by sliding the component along the grooved tract at the head of the board to the desired position and screwing it snugly into place. A rod extends perpendicularly from the attached component, and is adjustable through more than 90 degrees relevant to the board, so that the proper angle for optimal traction may be achieved. A patient requiring traction will have a halo ring, described above, surgically attached to his/her skull using standard skull pins. Such a halo ring allows for precise, adjustable manipulation of the head relative to the torso, thereby providing cervical reduction and maintenance of the reduction. If desired, the halo will be fitted with two head blocks in the standard position. To apply traction, the present invention's traction bale will be attached to the halo ring at either side of the head block attachments. A flexible line tied to the traction bale is fed along a groove in the traction rod and through a ring at the end of said rod. Appropriate weights then may be attached to the end of the line and hung over the head of the board until sufficient traction force has been applied to reduce the cervical spine fracture.

To achieve cervical immobilization on the board of this invention, a patient is similarly fitted with a prior art halo ring and head blocks. The cervical immobilization component of this invention is slid along the tract housing, either at the head of the board or on the board's sides, to the desired position and screwed tightly into place. Preferably, two cervical immobilization components are fitted to the board so as to provide maximum rigidity to the cervical immobilization by securing each halo head block to a separate component. A vertical post extends from each clamp component, perpendicular to the board. One or two rods, depending upon physician preference, is attached horizontally to each halo head block, and extended to the vertical post component. Using block clamp fittings, each horizontal rod is securely fixed to the vertical post in the position needed to optimally immobilize the patient's cervical spine in relation to the board.

When a patient in traction on the board requires cervical immobilization, the attachment of the invention's traction bale component directly to the halo ring allows the patient to remain in traction while the necessary cervical immobilization components are fitted to the halo head blocks. When these components are secured to the board and cervical immobilization is achieved, the traction components may be removed. With the patient's head and body securely immobilized, the patient can be safely and readily transported with the neck in the optimal position. No adjustments or instrumentation removals are necessary, and neck position may be rigidly maintained during any necessary tests or operations. If the preferred specifications and materials are used, the device will be compatible with standard radiographs, computerized tomography ("CT") scans, magnetic resonance imaging ("MRI"), and nuclear medicine testing, thereby enhancing the physician's access to the most advanced imaging techniques while maintaining cervical alignment without requiring transfer from stretcher to radiographic machine.

While cervical alignment can be maintained with the device of this invention during diagnostic tests, it is also useful in performing surgery. Cervical operations, to decompress the spinal cord or to fuse the cervical vertebrae, are facilitated because the board may be placed directly on the operating table. This allows maintenance of the radiographically directed cervical reduction, while facilitating surgical procedures by providing unencumbered access to the neck. The radiolucency of the board facilitates implantation of devices that often require radiographically guided placement. With the patient under general anesthesia, as is standard practice for any major surgical procedure, the body straps can be removed, thereby providing ready access to the remainder of the body for bone graft harvesting for cervical fusions or for other surgical procedures that are commonly necessary in the multiply injured trauma patient.

The patient may be placed in cervical immobilization on the board in either a prone or supine position. Should it be desirable to turn the patient or to allow ambulation, the patient may be fitted with a known halo vest without loss of cervical immobilization by sequentially replacing the horizontal rods which attach the halo head blocks to the board with support rods which attach the halo head blocks to a halo vest fitted about the patient's torso in the usual manner. Then the patient may be safely turned and reattached to the board, or may be allowed to ambulate, as the patient's condition dictates.

BRIEF DESCRIPTION OF THE DRAWINGS

These and other objects and advantages of the present invention will become more clearly apparent in connection with the following detailed description of a preferred embodiment, taken in conjunction with the appended drawings in which.

DETAILED DESCRIPTION OF A PREFERRED EMBODIMENT

Figure 1:
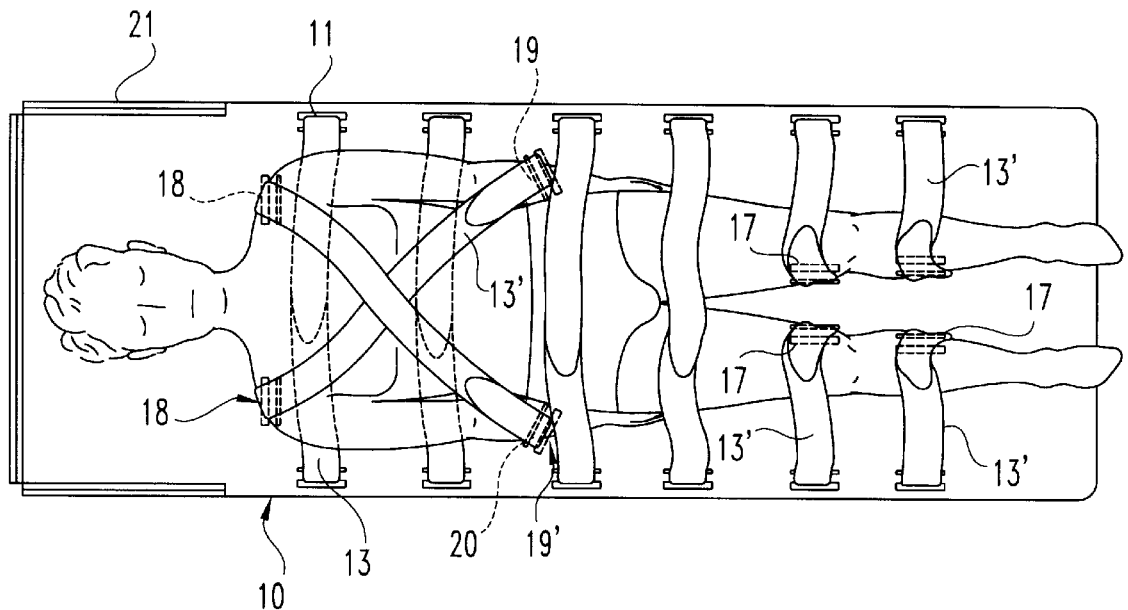
FIG. 1 is a plan view of a board according to the present invention showing a patient secured with straps, which view also shows the integrated tract that extends along the top edge of the board and continues along each side edge of the board for approximately 18–24 inches.

Referring initially to FIG. 1, a transportable, diagnostic and surgical procedure device that is constructed in accordance with the present invention is illustrated as a board designated generally at 10. In a preferred form, the board 10 comprises an elongated, preferably flat, rigid board which has a length and width in excess of the height and width of most individuals, whereby an individual or patient, as indicated in FIG. 1, may lie along the upper surface of the board. Board 10 has a head end adjacent the head of the patient and opposed sides adjacent the sides of the patient. Preferably, the width of the board does not exceed the maximum dimensions allowable for use of the board in common radiographic imaging equipment, including CT scans, MRI, fluoroscopy, and X-ray machines. The board is constructed of an expanded inner foam core and an outer shell of an acrylic resin laminate, which may be reinforced with carbon, fiber, Kevlar and woven glass. Alternatively the board can be molded from a resinous plastic material such as polycarbonate or modified phenylene oxide, although any non-porous, radiolucent, rigid, relatively light-weight material (e.g. laminated wood) would be acceptable for construction.

Figure 2:
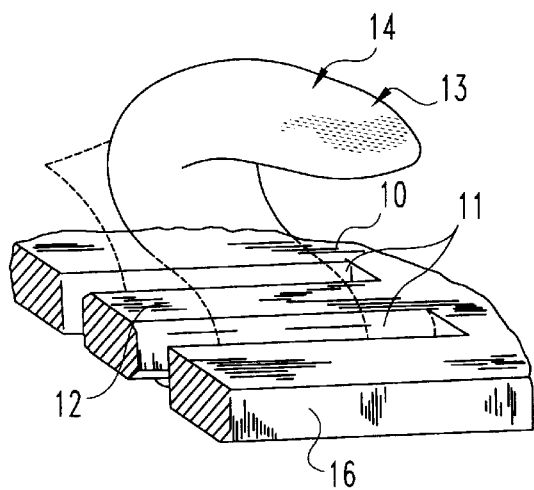
FIG. 2 is a fragmentary enlarged view of a longitudinal edge portion of the board shown in FIG. 1 showing straps received in slots.

A plurality of longitudinally spaced slots 11 are integrally formed along the outer side margins of the board 10 at evenly spaced locations therealong. As shown in FIG. 2, each pair of the slots 11 define a bar 12 extending centrally therebetween so that a flat strap 13, preferably made of woven nylon or other washable, flexible, durable, inelastic and mechanically strong material, may be guided around the bar 12. The straps 13 are of a sufficient width to minimize patient skin injury when they are tightened. One side of the end of strap 13 is covered with a Velcro-type fastening means of opposing hooks and loops at appropriate locations near the tip of strap 13 to allow the strap to be firmly affixed to itself after it has been guided around bar 12 simply by pressing the portion of the strap that is covered with hook fasteners 14 into the portion of the strap that is covered with loop fasteners 15. In this manner, a plurality of straps 13 can be affixed to the slots 11 in the board quickly and firmly to provide a means to secure the patient to the board. In order to immobilize the body of a patient lying on board 10, the straps 13 are secured to bars 12 between the slots 11 as described above. Then each strap 13 is extended across the patient's body and secured in position by overlaying the end of one strap 13 with the opposite end thereof, which comes up from the opposite side of the board. It will be appreciated that such ends will be covered with hook and loop fasteners of the Velcro-type which join to one another when pressed together.

Figure 3:
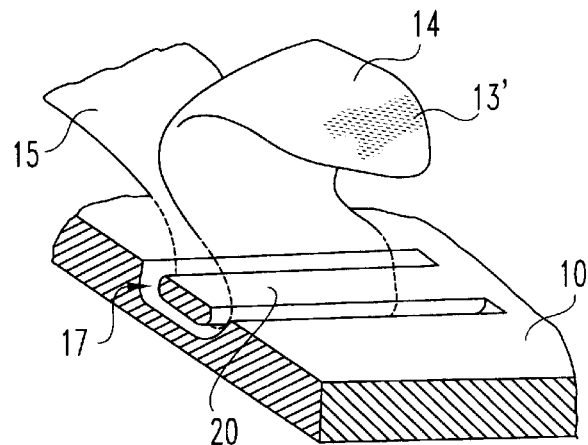
FIG. 3 is a fragmentary view of the board's interior strap fixation bars.

The space between bar 12 and the outer portion 16 of the slot 11 preferably is sufficiently wide and long to allow the portion to be gripped by the hands of individuals carrying the board 10. The outer portions 16 thus are of the appropriate size to be used as handholds, whereby the board 10 with an individual lying thereon may be picked up and transported. Two or more sets of interior slots 17 are molded or cut into the board 10 as shown in FIG. 1 to allow the straps 13 placed across the patient's lower extremities to secure each of the patient's legs separately, if desired, as shown in FIG. 1. Interior slot 17 is molded or cut into the board 10 as shown in FIG. 3. To secure a patient's leg, strap 13' is anchored in slot 11 as previously described, then passed over the leg, fed through the interior slot 17 and secured around a bar 20 as illustrated in FIG. 3. Strap 13 is pulled comfortably snug around the patient's leg and secured by pressing the hook fasteners on the tip of the strap into the loop fasteners which are attached to the strap at the appropriate point thereon. Additionally, two pairs of interior shoulder slots 18 are molded or cut into the board 10 at points corresponding with the likely position of the patient's shoulders on the board. A strap 13 is secured to the bar 20 of each pair of these interior shoulder slots, using the straps' hook and loop fasteners as described above. Once secured the two shoulder straps are crossed over the patients chest and fed through interior slots 19 which are molded or cut into board 10 at points and at an angle intended to accommodate the straps arising from the shoulder slots 18 in a manner to optimize the security of patient immobilization when the straps are tightened around bar 20 and fastened to themselves using hook fasteners 14 and loop fasteners 15. The approximate positioning of interior slots 17 and 19, as well as interior shoulder slots 18 with their corresponding straps 13 and 13', is shown in FIG. 1. It will be understood that these straps not only augment the immobilization provided by the transverse straps, but they also prevent movement of the patient's body toward the head of the board while cervical traction or immobilization is employed.

Figure 4:
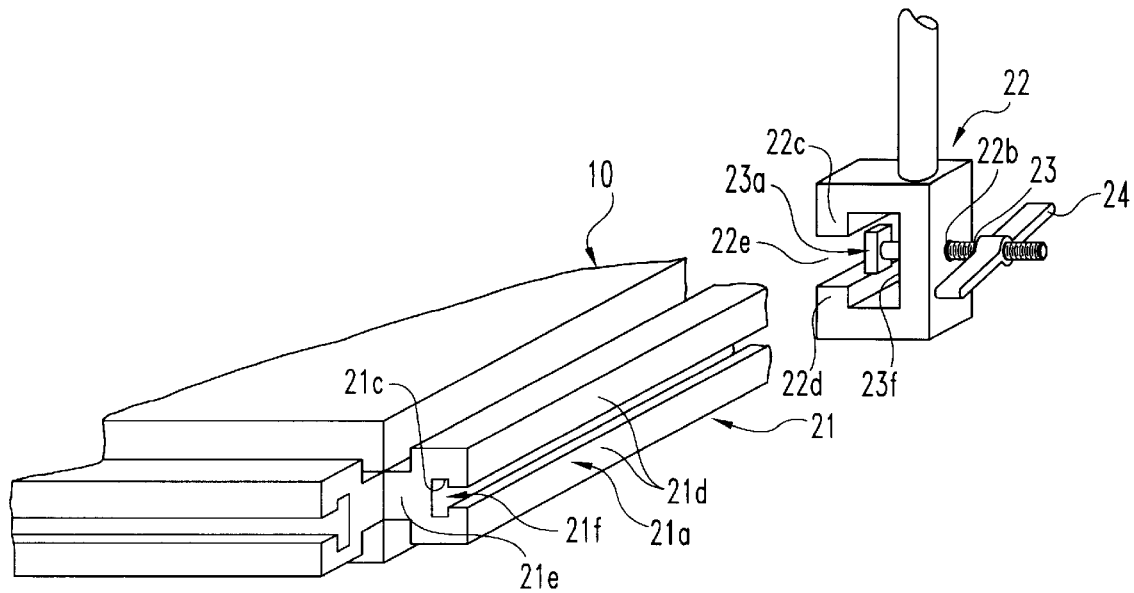
FIG. 4 is a fragmentary, perspective view of the upper left corner of the board, showing the integrated tracks and a component clamp which may be slid into the board's tracks and tightly secured thereto.

Extending along the entire length of the edge of the head of board 10, and extending approximately eighteen to twenty-four inches from the head of the board along both longitudinal edges thereof, is a grooved track 21 as shown in FIGS. 1 and 4. Track 21 serves as a channel to couple the clamp 22, as illustrated in FIG. 4. In a preferred embodiment, the track 21 is formed as a molded, integral part of the board 10. Alternatively, track 21 can be separately formed of any rigid, non-ferromagnetic material, such as graphite, that is sufficiently strong to provide a rigid, firm support for the attachment of track 21. The track 21 can be attached to the board 10 by any conventional means, such as by screws or permanent adhesives. In any case the track 21 includes an elongated rectangular block 21a having a T-shaped recess 21b extending longitudinally therethrough, and has planar inner and outer surfaces 21c and 21d. The clamp 22 consists of a "C" shaped member made of graphite, plastic or other like rigid, non-ferromagnetic material, with a screw 23 having a square head 23a extending through a threaded hole 22b in the body of clamp 22. Clamp 22 has upper and lower shoulders 22c, 22d that are separated by a recess 22e having a slightly greater vertical dimension than the flange 21e of the track 21. The track 21 has an internal longitudinal "T-shaped" recess 21f sized to slidingly receive the head 23a of the bolt 23. The clamp 22 is attached to track 21 by sliding it onto the track with the head 23a in the recess 21f to a desired position at any point along the track. Once the clamp 22 has been positioned as desired, the wing nut 24 is tightened by hand and to pull the head 23a back against the outer walls of the recess 21f, which pushes the wall surface 23f against the track surfaces 21d to clamp the element 22 in the desired position and preventing sliding thereof along the track 21. In fixed position, the upper and lower surfaces of clamp 22 are approximately co-extensive with the upper and lower surfaces of the board 10.

Figure 7:
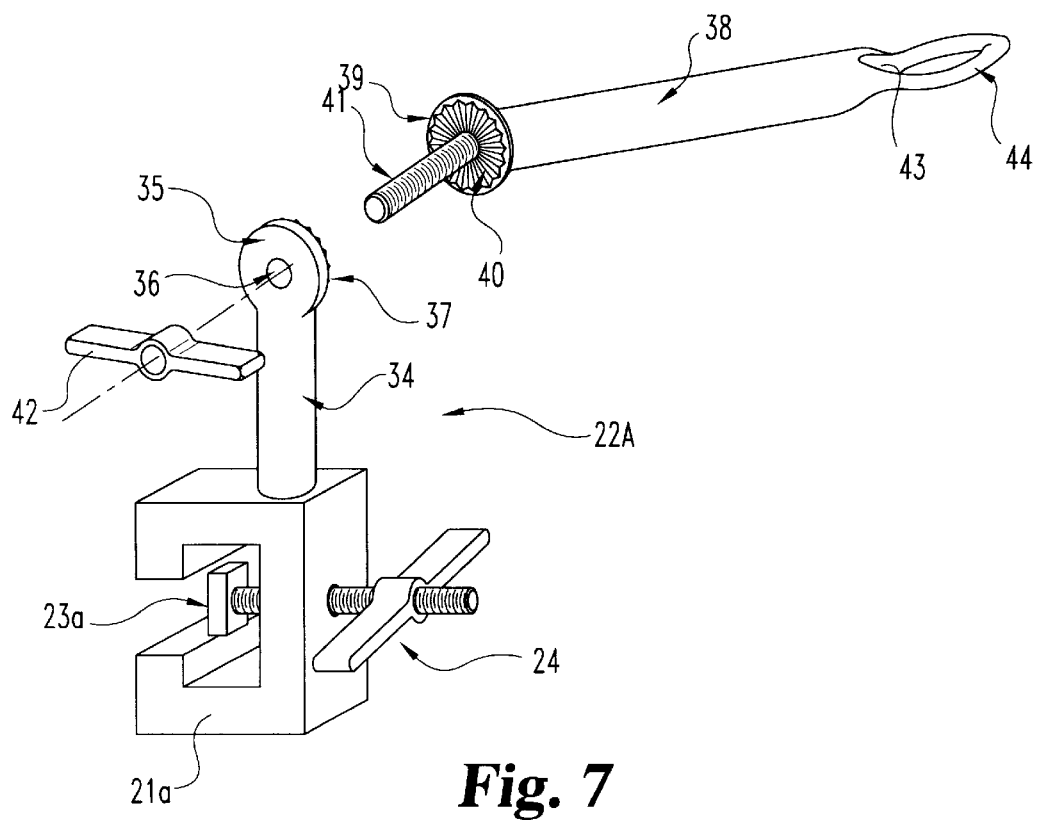
FIG. 7 is an exploded view of a clamp and arm assembly used to apply traction to a patient.

The clamp assembly 22 can take several forms and be included in arrangements that provide either cervical immobilization or cervical traction to a patient that is secured on the board 10. As shown in FIG. 7 in a form adapted for providing cervical traction; the clamp 22A supports a short post 34 that extends upward perpendicularly to the upper surface of the clamp. The upper portion of the post 34 is formed as a disc 35 having a center hole 36, the disc 35 also being perpendicularly to the top edge of the clamp 22A when it is properly mounted in track 21. The disc 35 has radial teeth 37 to permit angular adjustment of a traction arm 38 having a companion disc 39 on the inner end thereof. Disc 39 is similarly equipped with radial teeth 40, and a threaded screw 41, which fits through central hole 36, and is tightened into place with wing nut 42. By rotating the disc 39 relative to disc 35 before tightening the wing nut 42, the arm 38 can be oriented at various angles that might be appropriate for securing the traction cable. Traction arm 38 is equipped with a groove 43 along its anterior or upper edge of sufficient width and depth to guide the traction cable into and through a guide or ring 44 which is integral with the outer end of the rod.

Figure 8:
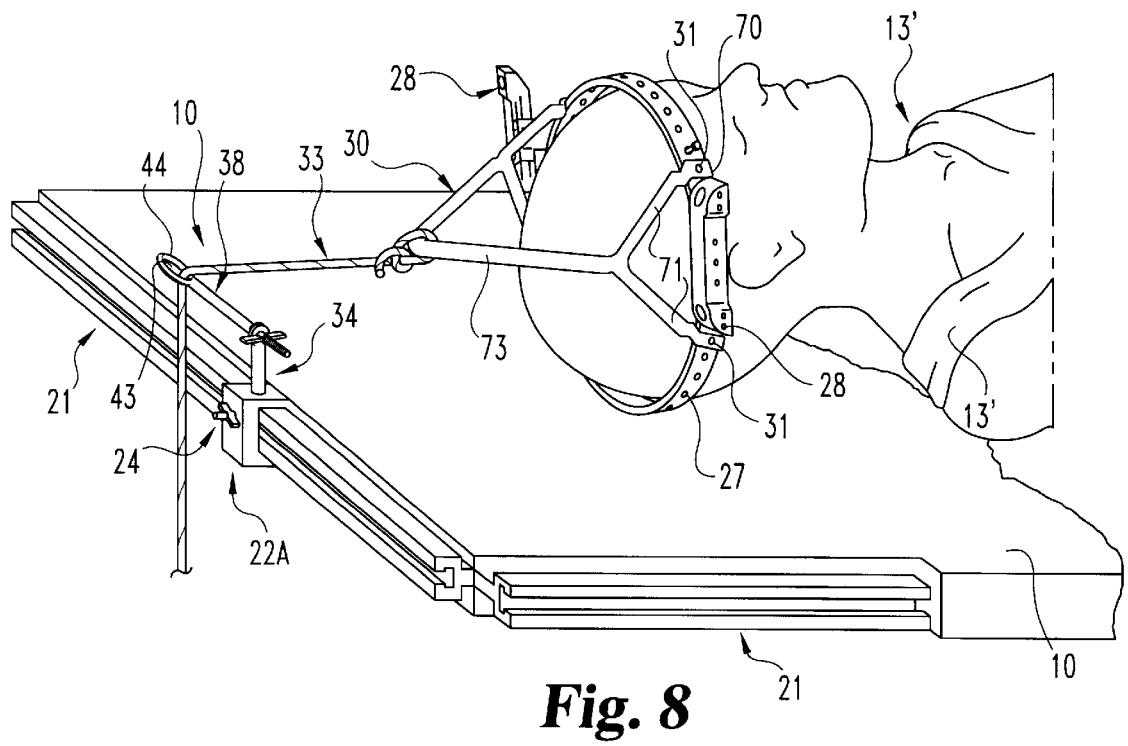
FIG. 8 is a fragmentary perspective view of a patient fitted with the traction assembly using a halo ring and a traction bale in accordance with the invention.

As shown in FIG. 8, a patient lying on the board 10, and who has need of cervical traction, is first securely strapped to the board using straps 13 and 13' as described above. A halo ring 27, with or without head blocks 28, is then surgically attached to the patient's skull in the usual manner. In accordance with this invention, a bale 30 is attached to the halo ring 27 at halo screw holes adjacent to those occupied by the head blocks 28 on either side of the halo ring 27. The bale 30 is made of graphite, plastic or similar rigid, strong, non-ferromagnetic material and has four end sections or brackets 31 which contain screw holes in which pins are inserted to tighten the bale to the halo ring 27 so as to position each section 31 adjacent to the halo head block 28, if such is present. Each section 31 has a tang 70 that curves inward on the bottom side of the halo ring 27 to maintain a secure connection of the bale 30 to the halo ring. Bale sections 71 incline towards one another and join at an apex as shown, and a V-shaped pull section 73 extends outward from the apexes. The design provides a traction vector that originates from approximately the center of the head of the patient, while allowing simultaneous attachment of the head blocks 28 that may be used to couple the patient's head to the immobilization board 10 and/or a halo jacket when traction is removed. This allows for a smooth transition from traction to rigid immobilization, thereby minimizing neck movements while switching between traction and rigid immobilization.

Clamp 22A is positioned on the head end of the board in the desired location and tightened into place. Arm 38 is adjusted to an angle appropriate for applying axial force needed to reduce the patient's cervical fracture and tightened. A traction cable 33 is tied or otherwise secured to the outer apex of the bale section 73, and is fed along the groove 43 in traction rod 38 and through the cable guide 44. The cable 33 then is allowed to extend over the edge of board 10 where its free end is attached to a standard weight stand which can accommodate several different values of weights so that appropriate weight amount may be added until the desired traction force is achieved.

Figure 5A:
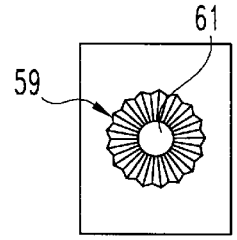
FIG. 5A is a front view of a clamp block used to orient a rod as desired.
Figure 5:
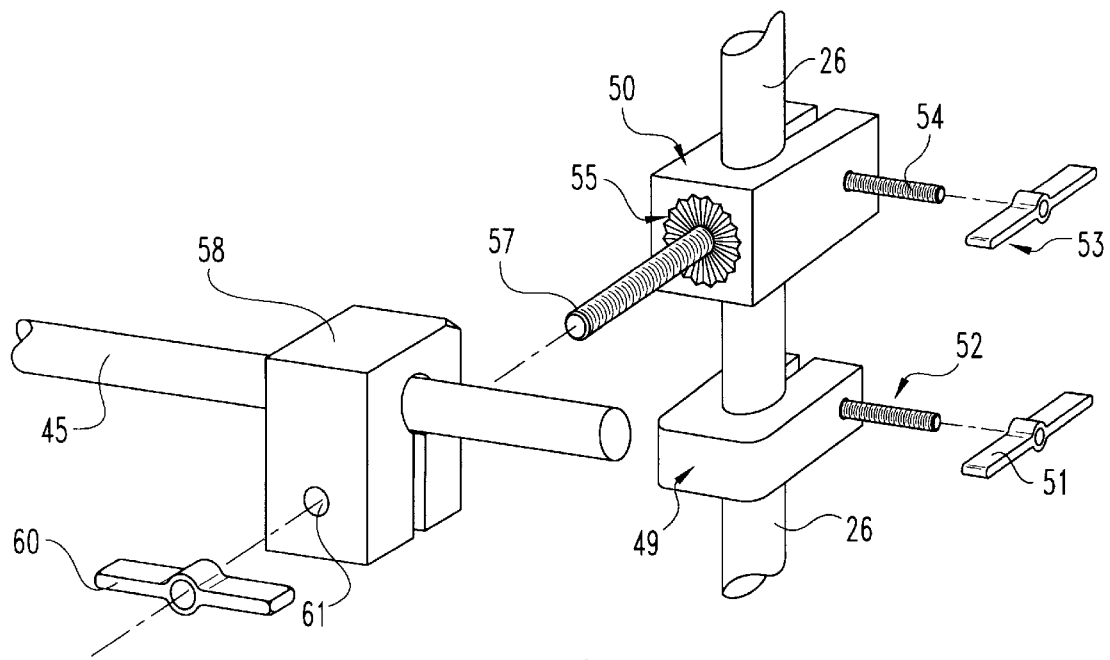
FIG. 5 is an exploded, perspective view of the clamps used to secure the vertical rod attached to the component clamp shown in FIG. 4 with the horizontal rod that will be attached to a patient's halo head block so as to produce rigid cervical immobilization.
Figure 6:
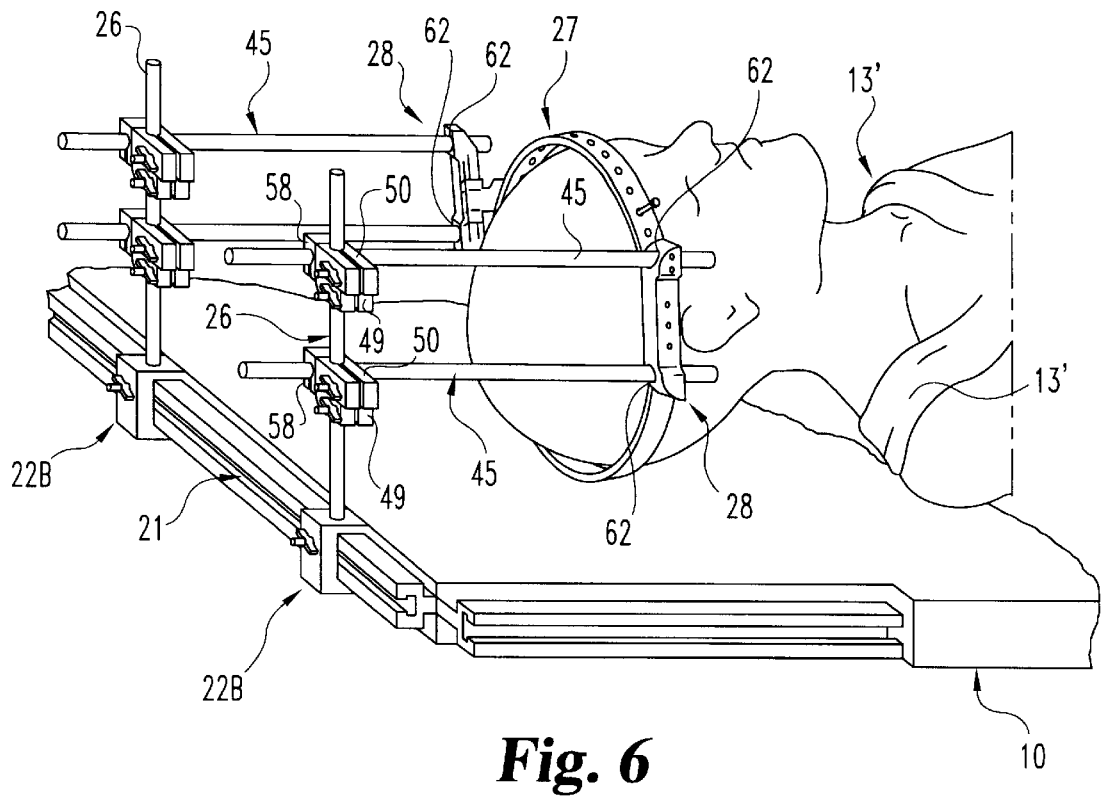
FIG. 6 is a fragmentary perspective view of a patient in cervical immobilization on the board utilizing horizontal rods on the patient's left side and right sides.

Another configuration indicated as 22B of clamp 22 is shown in FIGS. 5 and 6 and functions as a vertical support assembly in providing cervical immobilization to a patient on board 10. As illustrated, the clamp 22B includes a body like the element 22, described above, which mounts a straight rod 26 that extends upward perpendicularly from the upper surface of such element. When a patient is to be placed in cervical immobilization, the patient is placed on the board 10 and secured with the straps 13 and 13' as described above. Then a halo ring 27 is surgically fitted to the patient's skull in a typical manner. Two head blocks 28 are attached to the halo ring also as described above. The element 22B is slid along track 21 until it is in the desired position, and then is tightened in place, as described above. The upright post 26 is fitted with a standard split block clamp 49 and another split block clamp 50, as shown in FIG. 5. The clamp 49 is used to set the desired vertical height for a cervical immobilization rod 45, and is slid down the upright post 26 to the desired position and locked in place by tightening a wing nut 51 along a threaded stud 52 to pull the opposing sides of clamp 49 together, thereby tightening the clamp 49 around the upright post 26 and preventing sliding movement. Next split block clamp 50 is positioned on vertical bar 29 to rest on top of clamp 49. Clamp 50 may be rotated around the upright post 26 until the desired flexion and extension angle for fixing a horizontal support bar 45–48 is achieved. The clamp 50 then is secured in place by tightening the wing nut 53 along the threaded stud 54 to pull the opposing sides of clamp 50 together, thus tightening the clamp 50 around the upright post 26 to prevent sliding movement.

Clamp block 50 has a circular disc 55 affixed to it which, as shown in FIG. 5, has radial teeth. A threaded rod 57 extends from the center of the disc 55. Another split clamp block 58 is similarly equipped with a circular disc 59 (FIG. 5A) having radial teeth, and a bore 61 passes through the center of such disc. The threaded rod 57 is inserted through bore 61 to attach clamp block 58 to clamp block 50 which are fixed in a certain relative orientation when the wing nut 60 is tightened.

Since the clamp blocks 49, 50 and 58 are all split block attachments, they have multiple degrees of freedom to allow alteration of the patient's head position in all planes. This design also allows single or multiple horizontal rod assemblies to be placed on the upright post 26, in order to accommodate the preferred combination of horizontal support bars, as will be described further below.

Figure 9A:
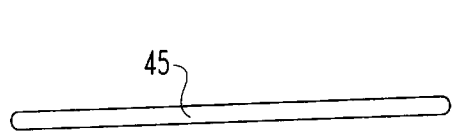
FIG. 9A shows a rod that can be used as the horizontal component described in FIG. 6 when the vertical rod is attached to a component clamp that is secured to the integrated tract at the end of the board.
Figure 9C:
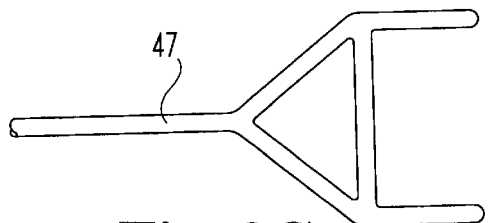
FIG. 9C is a view of another rod assembly having upper and lower sections and a spreader component.
Figure 9B:
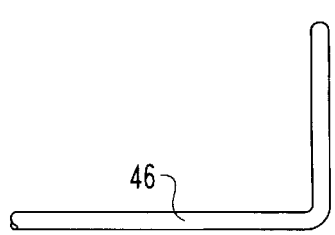
FIG. 9B is a view of a different rod that can be used as the horizontal component when the vertical rod is attached to a component clamp that is secured to the integrated tract at the side of the board.
Figure 9D:
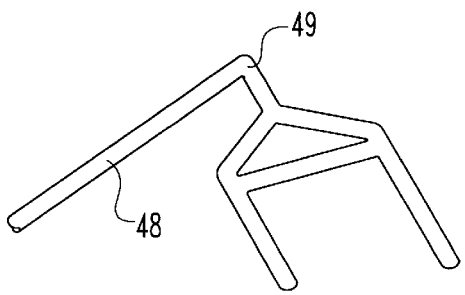
FIG. 9D shows a rod assembly similar to FIG. 9C but with the outer rod bent at an angle to allow side clamping.

After clamp 22B and the upright post 26 are fitted with clamps 49, 50 and 58, a proper horizontal support bar is selected. As disclosed herein, the invention offers a choice of four (4) different horizontal support rods: rod 45 shown in FIGS. 9A which is a straight cylindrical rod; rod 46, shown in FIG. 9B which is a cylindrical rod with a single right angle bend; rod 47 shown in FIG. 9C which is a cylindrical rod that bifurcates or branches into two cylindrical rods or rod portions, which branches are spaced such that the branching rods can be inserted and fixed into the two holes of a halo head block in the standard manner; and rod 48, shown in FIG. 9D that is essentially identical to rod 47 except that is has a single right angle bend at 49 in the single cylindrical rod. Regardless of the horizontal support bar selected, it is fitted to the halo head block 28 and to clamp 58 in the same manner, which is as follows: The distal end of a horizontal support bar 45–48 is inserted into the holes 62 (FIG. 6) of the head block 28, which holes are designed to receive the support bars which fix the position of the halo 27 when cervical immobilization is applied. In the case of bars 47 or 48, the end with the two branched bars is inserted into holes 62 and the opposite end of the horizontal support bar is inserted through the clamp 58. When the desired longitudinal position of the bar is achieved, it is fixed in position by tightening wing nut 60 on the threaded rod 57, as described above and shown in FIG. 6. The design of the various clamps 49, 50, and 58, as well as the design of the base clamp 22B, allow the components to be loosened slightly to make needed positioning adjustments with respect to the horizontal support rod. Each adjustment can be made infinitely small and over an appropriate range of adjustability, and can be made without degradation of other adjustments.

Figure 10:
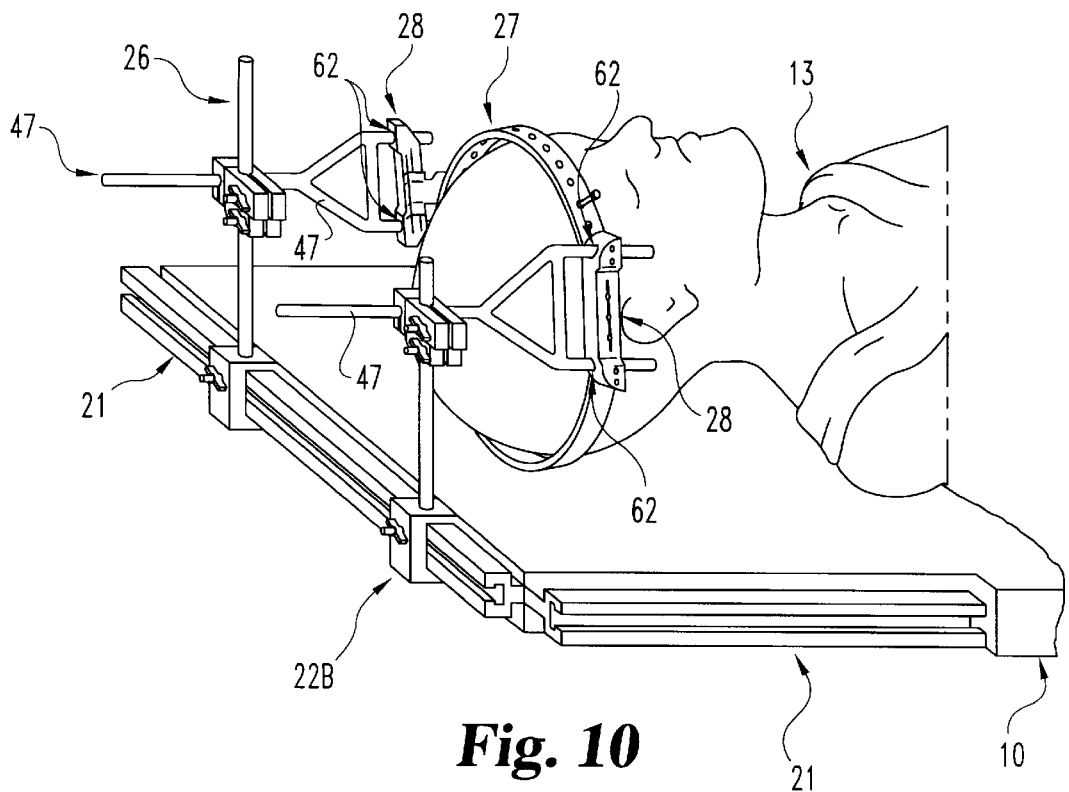
FIGS. 10 and 11 are perspective views showing various ways the rods are used to hold a halo attached to a patient's head.
Figure 11:
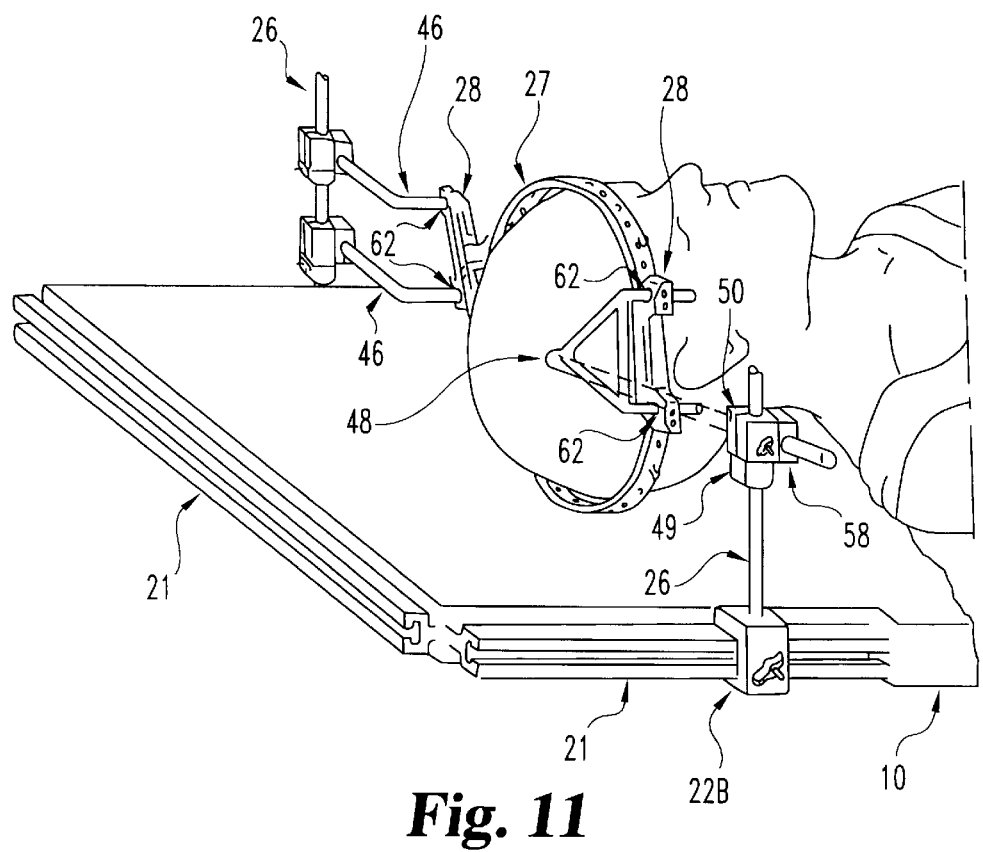

The differing features of the support rods 45–48 allow the clamp 22B to be fitted in track 21 either along the head of the board 10 or on the tracks along its longitudinal sides. Should a support rod 45 or 47 be selected, clamp 22B would be fixed on track 21 at the head of board 10. The support rods would then be attached to the vertical bar 26 of the clamp 22B, as described above, to fix the patient's cervical immobilization. The use of rod 45 is illustrated in FIG. 6, while rod 47 is shown in FIG. 10. If either of the support rods 46 or 48 are chosen to attain cervical immobilization, a clamp 22B would be attached to track 21 located along the sides of board 10 to secure the rods 46 or 48, as illustrated in FIG. 11. The interchangeable nature of horizontal support rods 45–48 allows great flexibility in the configuration of a patient's cervical immobilization. For example, if access to the top of the patient's head is needed for a surgical procedure, or for other reasons, the use of the rods 46 or 48, which are anchored to the sides, will provide such access. It will be appreciated that multiple other combinations of the horizontal support bars 45–48 are possible.

A patient in cervical traction on the board 10 may easily be placed in cervical immobilization without disengaging the traction device until such immobilization is complete which greatly reduces the risk that cervical alignment achieved by the traction will be lost when transferring the patient to cervical immobilization. To attain cervical immobilization, the patient in traction has the appropriate number of horizontal support bars 45–48, or a combination thereof, affixed to the halo head block 28. Two clamps 22B are positioned along track 21, as desired, and clamps 49 and 50 are mounted on upright post 26, as described above. Then the selected horizontal support bars are slipped through clamps 58, and the clamps are secured to clamps 50 and adjusted as required to achieve optimal alignment for the desired angle of cervical immobilization. Once cervical immobilization is fixed, the traction bale 30 and other components used to impart traction can be removed from the patient.

The cervical immobilization components of the present invention also can be used to secure a patient during surgery. The patient can be secured in either a supine or prone position, with cervical immobilization constantly maintained and with free access available to the patient's body.

It also is possible for the clamps 22A and 22B to be affixed directly to a table or an available spine board. A C-shaped coupling device could accomplish this coupling anywhere along the length of the board. However this type of coupling mechanism is less desirable than that described herein because the coupling would not lie flush with the bottom of the board, and the mechanical strength of the coupling would be less. These factors would make accidental dislodgment more likely.

It now will be recognized that a new and improved transportable cervical immobilization device or assembly has been disclosed and which meets all the objectives of the present invention. It is to be understood that the invention is not to be limited to the disclosed embodiment, but on the contrary, is intended to cover various modifications and equivalent arrangements included within the spirit and scope of the appended claims.

What is claimed is:

1. A transportable, diagnostic and surgical procedure device comprising:

a rigid board having a length and width in excess of the height and width of a typical patient and compatible with radiographic imaging devices, said board having a head end and opposed sides;

means for securing a patient to the board;

track means secured to said board suitably adapted for use in the attachment of components by which a patient is placed in cervical traction or cervical immobilization, said track means including a first track extending along said head end and oppositely disposed second and third tracks on opposite sides of said board adjacent said head end, each of said tracks having a longitudinal slot; and clamp means constructed of a rigid, non-ferromagnetic material and having a body formed to fit on said track means at a predetermined position; and adjustable means on said body for fixing it to said track means in said predetermined position.

2. The device of claim 1 wherein said slot has a T-shaped configuration, said adjustable means having a head adapted to be received in said configuration, and means for tightening said head in said slot.

3. The device of claim 2 further including an upstanding post on said body, and additional clamp means on said post for fixing a horizontal rod thereto which extends to a halo ring on the patient's head.

4. The device of claim 3 wherein the rod is straight.

5. The device of claim 3 wherein the rod has a single right-angle bend.

6. The device of claim 3 wherein the rod is bifurcated on one end.

7. The device of claim 3 wherein said rod is bifurcated and has a right-angle bend.

8. The device of claim 3 wherein said post has circular means on its upper end forming radial teeth, and further including an arm having a guide on one end and circular means on its other end adapted to engage said circular means on said post; and means for securing said circular means and radial teeth together with said post and arm in a selected circular orientation.

9. An arm assembly made of durable, rigid material and adapted to guide a traction member used during the application of traction force to the cervical spine of a patient comprising:

an upstanding post having a first circular disc mounted at its upper end, said first disc carrying a central threaded screw and having radial teeth, an arm having a second circular disc on one end, said second disc having a central hole and radial teeth, said hole adapted to receive said screw;

nut means on said screw for engaging said radial teeth with said arm in a selected angular position; said arm having a groove in its upper edge of sufficient width and depth to guide a traction cord; and a ring on the outer end of said arm through which said cord passes.

10. A method of placing a patient in traction, while allowing simultaneous attachment of halo head blocks, which head blocks may be used to secure the patient in cervical immobilization, thereby minimizing neck movements while switching between traction and rigid cervical immobilization, comprising the steps of:

placing the patient on a rigid, substantially flat, transportable board which has means for attaching the appropriate traction components;

placing a halo ring on the patient's head;

securing the patient's body to said board to prevent undue movement while in traction;

securing a traction bale having a plurality of attachment points to the halo ring;

securing a cable guide component to the head end of the board on which the patient is lying at a position substantially inclined with the patient's head, said cable guide component having an adjustable arm with a cable guide on its outer end;

positioning said arm at an angle appropriate for applying axial force needed to reduce the patient's cervical fracture;

securing a traction cable to the bale;

feeding the traction cable through said guide so that said cable hangs freely over the end of the board on which the patient is secured; and attaching selected weights needed to reduce the patient's cervical fracture.

11. A combination of clamps used to affix a horizontal support bar to a clamp on an edge of a board, comprising:

an upright post on said clamp;

a first split block including means to fix it to said post to provide a vertical stop;

a second split block including means to fix it to said post above said first split block, said second split block having a circular disc on one side with a threaded rod extending perpendicularly from its center, and radial teeth emanating from said rod; and a third split block including means to fix it to a support rod emanating from the head blocks of a halo ring, said third block having a circular disc on one side, a bore in its center, and radial teeth surrounding said bore, said teeth and threaded rod allowing said third block to be firmly affixed to said second block at a selected orientation.

12. A method of fixing a patient in cervical immobilization, comprising the steps of:

placing the patient on a rigid, substantially flat board having means for attaching cervical immobilization components;

securing the patient's body to the board by means adapted to prevent undue movement while in cervical immobilization;

placing a halo ring on the patient's head;

fitting the halo ring with two head blocks;

securing cervical immobilization clamps at selected positions on the board on which the patient is lying;

securing horizontal support bars to the halo head blocks, such that the support bars extend outwardly of the patient's head; and fixing said horizontal support bars in place between said head blocks and said clamps at selected angles of support.

13. A device for providing medical treatment to a patient, comprising:

(a) a rigid board having a length and width in excess of the typical height and width of the patient and being configured to carry the patient, said board having a head end;

(b) a track carried by said board at said head end;

(c) a number of straps to secure the patient to said board;

(d) a clamp engaging said track and being selectively positionable therealong, said clamp being configured for fixation in a selected position along said track;

(e) a post extending from said clamp upward from said board, said post being maintained in a fixed relationship relative to said board by said clamp when said clamp is fixed in said selected position; and (f) an arm configured to fasten to said post at a selected angular position relative to said post, said selected angular position being variable over a range of angles, said arm having an outer end extending away from said post, said outer end defining a ring for engaging a traction component coupled to the patient's head.

14. The device of claim 13, further comprising:

(g) a traction halo configured to engage the patient's head; and (h) a traction cord coupled to said halo and passing through said ring of said arm.

15. The device of claim 14, further comprising a bale coupled between said halo and said traction cord to provide a traction vector, said bale including two sections joined in a V-shaped apex.

16. The device of claim 13, further comprising a nut, and wherein:

said post includes a first disc defining a first number of radial teeth and defines a hole through said first disc;

said arm includes a second disc defining a second number of radial teeth and a threaded screw; and said first teeth are configured to engage said second teeth in a fixed rotational position corresponding to said selected angular position when said nut is tightened on said threaded screw extending through said hole.

17. The device of claim 13, wherein said clamp has a C-shaped member configured to slidingly engage said track, said clamp carrying a bolt with a head configured to engage a T-shaped recess defined by said track.

18. The device of claim 17, wherein said bolt extends through a hole defined by said C-shaped member and includes a nut threaded on said bolt opposite said head to fix said clamp to said track when said C-shaped member engages said track, said head engages said T-shaped recess, and said nut is tightened on said bolt.

19. A device for providing medical treatment to a patient, comprising:

(a) a rigid board having a length and width in excess of the typical height and width of the patient and being configured to carry the patient;

(b) a first track carried by said board;

(c) a number of straps to secure the patient to the board;

(d) a first post configured for selective fixation along said first track to extend upward from said board;

(e) a first support rod configured to extend between the patient's head and said first post;

(f) a first clamp adjustably engaged to said first post in a selected translational position therealong; and (g) a second clamp adjustably engaged to said first support rod, said second clamp being engaged to said first clamp in a selected rotational position relative to said first clamp.

20. The device of claim 19, wherein said first clamp and said second clamp each include a split block, rotational position of said first clamp about said first post is selectable, and translational position of said second clamp along said first support rod is selectable.

21. The device of claim 19, further comprising:

(h) a second support rod configured to extend between the patient's head and said first post;

(i) a third clamp adjustably engaged to said first post; and (j) a fourth clamp adjustably engaged to said first support rod and said third clamp.

22. The device of claim 19, further comprising a third clamp engaging said first post below said first clamp.

23. The device of claim 19, further comprising:

(h) a second track carried by said board;

(i) a second post configured for selective fixation along said second track to extend upward from said board;

(j) a second support rod configured to extend between the patient and said first post;

(k) a third clamp adjustably engaged to said second post; and (l) a fourth clamp adjustably engaged to said second support rod and said third clamp.

24. The device of claim 19, further comprising a third clamp configured to fix said first post along said first track, said third clamp having a C-shaped member configured to slidingly engage said track and carrying a bolt with a head configured to engage a T-shaped recess defined by said first track.

25. The device of claim 19, further comprising a nut, and wherein:

said first clamp defines a first number of radial teeth and threaded rod extending therefrom; and said second clamp defines a second number of radial teeth and a hole therethrough; and said first teeth are configured to engage said second teeth to provide said selected rotational position when said nut is tightened on said threaded screw extending through said hole.

* * * * *